United States Patent [19]

Hay et al.

[11] Patent Number: 5,110,993
[45] Date of Patent: May 5, 1992

[54] 9,9-BIS(3,5-DIPHENYL-4-HYDROXY-PHENYL)FLUORENE AND POLY(ARYLENE ETHERS) THEREFROM

[76] Inventors: Allan S. Hay, 5015 Glencairn Avenue, Montreal, Quebec H3W 2B3; Zhi Y. Wang, 3600 Parc Ave., Apt. A 1803, Montreal, Quebec H2X 3R2, both of Canada

[21] Appl. No.: 653,079

[22] Filed: Feb. 8, 1991

[51] Int. Cl.$^5$ ............................................. C07C 39/17
[52] U.S. Cl. .................................. 568/721; 568/716; 568/717; 568/718; 568/719
[58] Field of Search ................. 528/725; 568/716, 717, 568/718, 719, 721

[56] References Cited

U.S. PATENT DOCUMENTS 3,723,465  3/1973  Hall et al. ............................ 260/328
4,889,909  12/1989  Besecke et al. ...................... 528/125

OTHER PUBLICATIONS

Wang et al. "Chem. Abst." vol. 115(4) p. 30042a (1991).
Hergenrother et al "Poly(arylene ethers)" POLYMER, 1988, vol. 29, Feb. pp. 358 to 368.
Webb et al "A New Reaction of 2-Phenylphenols with Carbonyl Compounds Yielding Dibenzopyrans", J. Org. Chem., vol. 38, No. 8, 1973, pp. 1621-1622.
Hergenrother et al "Poly(arylene ethers) From Bis-1,3 and 1,4-(4-Chlorobenzoyl)-Benzene", Polymer Prep. 1985, vol. 26, pp. 174-175.

Primary Examiner—Werren B. Lone
Attorney, Agent, or Firm—Bachman & LaPointe

[57] ABSTRACT

9,9-Bis(3,5-diphenyl-4-hydroxyphenyl)fluorene a novel compound can be used to produce amorphous poly(arylene ethers) which have high glass transition temperatures and good thermo-oxidative stability and which are soluble in aromatic and chlorinated solvents; the novel fluorene derivative is produced by transalkylation of 9,9-bis(4-hydroxyphenyl)fluorene or 9,9-bis(4-methoxyphenyl)fluorene with 2,6-diphenylphenol.

1 Claim, No Drawings

9,9-BIS(3,5-DIPHENYL-4-HYDROXYPHENYL)-FLOURENE AND POLY(ARYLENE ETHERS) THEREFROM

BACKGROUND OF THE INVENTION i) Field of the Invention

This invention relates to a novel fluorene derivative, 9,9-bis(3,5-diphenyl-4-hydroxyphenyl)fluorene and a novel transalkylation process for its preparation, as well as to novel poly(arylene ethers) derived from the novel fluorene derivative, and a process for the preparation of the poly(arylene ethers).

ii) Description of Prior Art

Poly(arylene ethers) are an important class of high performance thermoplastics having an attractive combination of chemical, physical and mechanical properties. Commercially available poly(arylene ethers) are used in a variety of applications as moulding resins, coatings, adhesives and ultra-filtration membranes; in addition poly(arylene ethers) have attracted considerable attention as potential matrix resins for advanced composites in aerospace vehicles.

A disadvantage of many known poly(arylene ethers) is that they lose their properties at relatively low temperatures because of their low glass transition temperatures, and in some cases they have poor thermo-oxidative stability.

U.S. Pat. No. 4,889,909 describes certain high temperature-resistant poly(arylene)ethers which are amorphous and which are thermoplastic.

Semi-crystalline poly(arylene ethers) have been described in Polymer, 1988, Vol. 29, pages 358 et seq P. M. Hergenrother et al; and both crystalline and amorphous poly(arylene ethers) have been described in Polymer Prep. 1985, Vol. 26, page 174 et seq, P. M. Hergenrother et al.

The acid-catalyzed condensation of carbonyl compounds, for example, ketones, with phenols to yield bisphenols is well known. If the ketone is aromatic, the dihalide derivative is employed in place of the ketone.

J. Org. Chem. Vol. 38, No. 8, 1973, 1621-1622, J. L. Webb et al confirms that 2,6-diphenylphenol will not react with acetone to form a bisphenol, but that under strong acid conditions a pyran is formed. U.S. Pat. No. 3,723,456 exploits the reaction to produce pyrans.

SUMMARY OF THE INVENTION

It is an object of this invention to provide a novel bisphenol which may be used to prepare poly(arylene ethers) of improved characteristics.

It is a further object of this invention to provide a novel process for producing the novel bisphenol.

It is still a further object of this invention to provide novel poly(arylene ethers) of improved characteristics; more especially amorphous poly(arylene ethers) which are solvent soluble at ambient temperature, have a high glass transition temperature (Tg) and display high thermo-oxidative stability.

In accordance with one aspect of the invention there is provided 9,9-bis(3,5-diphenyl-4-hydroxyphenyl)fluorene.

In accordance with another aspect of the invention there is provided a process of producing 9,9-bis(3,5-diphenyl-4-hydroxyphenyl)fluorene by transalkylating 9,9-bis(4-hydroxyphenyl)fluorene or 9,9-bis(4-methoxyphenyl)fluorene with 2,6-diphenylphenol.

In still another aspect of the invention there is provided novel poly(arylene ethers) having bulky cardo segments derived from 9,9-bis(3,5-diphenyl-4-hydroxyphenyl)fluorene.

In yet another aspect of the invention there is provided a method of producing the aforementioned poly(arylene ethers) of the invention by a nucleophilic substitution reaction.

DESCRIPTION OF PREFERRED EMBODIMENTS i) 9,9-Bis(3,5-diphenyl-4-hydroxyphenyl)fluorene The novel 9,9-bis(3,5-diphenyl-4-hydroxyphenyl)fluorene is represented by formula (I):

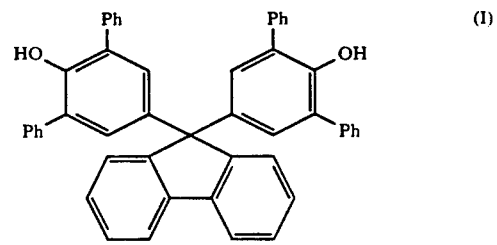

in which Ph is phenyl.

The compound (I) provides a bulky cardo group when used to form a segment of poly(arylene ethers) and as a consequence causes a significant increase in Tg while providing good solubility; the pendant phenyl groups on the fluorene segments in the backbone of a poly(arylene ether) provide increased thermo-oxidative stability along with increased Tg in the polymer.

The compound (I) is produced in high yield by the transalkylation of a fluorene of formula (II):

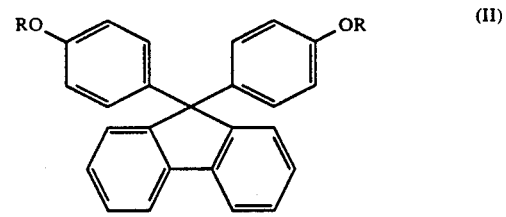

wherein each R which may be the same or different is a hydrogen atom or a methyl group, with 2,6-diphenylphenol. Preferably each R is the same.

Suitably the transalkylation is carried out by heating the reactants in the presence of a strong acid, for example, methane sulfonic acid.

The reaction can be represented by equation (I):

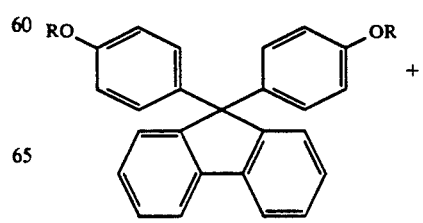

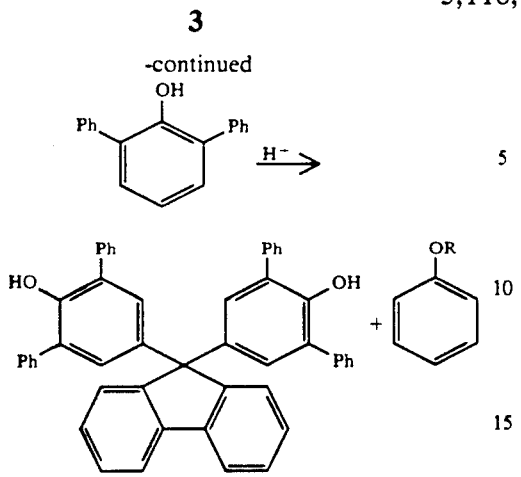

in which suitably each R is a hydrogen atom or a methyl radical.

The transalkylation reaction is found to produce the compound (I) in high yield, without formation of pyran compounds of the type formed when 2,6-diphenylphenol is heated under acidic conditions with ketones as described in U.S. Pat. No. 3,723,465 and by Webb et al (see previously).

The transalkylation is an equilibrium reaction and therefore the by-product phenol or anisole should be removed during the course of the reaction or a large excess of the 2,6-diphenylphenol can be employed.

In the case where R is a hydrogen atom and the by-product is phenol, the phenol is suitably removed from the reaction mixture by distillation under reduced pressure.

In a particular embodiment the 9,9-bis(4-hydroxyphenyl)fluorene and a two to three-fold excess of 2,6-diphenylphenol are heated in a high boiling solvent, for example, 1,2,4-trichlorobenzene in the presence of the strong acid, at a temperature of 70° to 85° C., preferably 75° to 80° C. under reduced pressure for a period of 12 to 24 hours, with adjustment of the vacuum so that only the by-product phenol is removed by distillation. The progress of the reaction can be monitored by TLC.

At completion of the reaction the organic phase can be separated from the acid, and can be poured into petroleum ether to precipitate the reaction product and unreacted 2,6-diphenylphenol.

The precipitated solids can be washed to remove unreacted 2,6-diphenylphenol; cyclohexane may be employed as the washing agent.

The compound (I) can be produced in this way in yields typically of 77 to 95%.

In the case where R is a methyl group the reaction conditions and purification conditions are simpler. In particular a lower reaction temperature and higher reduced pressure can be employed since the by-product anisole (bp 154° C.) has a lower boiling point than phenol (bp 182° C.).

Typically the fluorene (II) in which R is methyl is reacted with 2,6-diphenylphenol at a temperature of 55° to 70°, preferably 60° to 65° C. under reduced pressure; the reaction progress can be monitored by TLC.

An intermediate in the transalkylation is the mono-exchanged compound of formula (III):

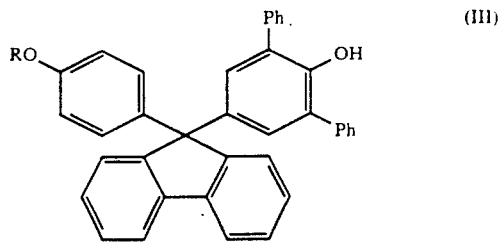

in which Ph is phenyl and R is a hydrogen atom or methyl group.

For the reaction in which R is a hydrogen atom recrystallization of the compound (I) is difficult due to contamination with the intermediate(III) in which R is a hydrogen atom, this compound not being easily separated. However, trimethylsilylation produces a silyl ether of compound (I) of formula (IV):

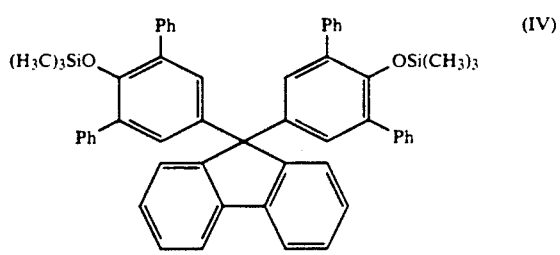

which can be readily purified by recrystallization from n-heptane and hydrolyzed to the compound (I) in high purity.

This latter purification step via the silyl ether is not necessary when R is a methyl group since the intermediate (III) in which R is methyl is easily removed in the precipitating and washing steps.

The fluorene (II) in which R is a hydrogen atom is available commercially, the corresponding compound in which R is a methyl group can be obtained by methylation of the 9,9-bis(4-hydroxyphenyl)fluorene with dimethyl sulfate under phase-transfer conditions as described in Tetrahedron, 1974, Vol. 30, page 1379, by McKillop et al.

ii) Poly(arylene ethers)

The poly(arylene ethers) which have segments derived from the compound (I) may be represented by the general formula (V):

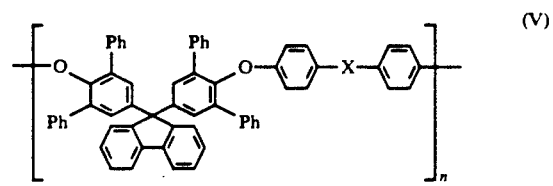

in which Ph is phenyl;
X is

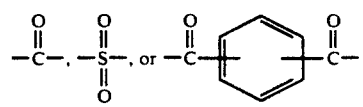

and n is an integer determining the molecular weight of the polymer and is typically greater than 20, usually 20 to 200, more usually 50 to 100.

When X is

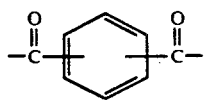

the carbonyl groups may be in 1,3 or 1,4 positions, i.e.,

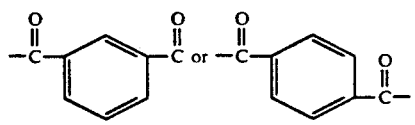

The poly(arylene ethers) of formula (V) are readily formed by nucleophilic aromatic substitution in accordance with equation (II):

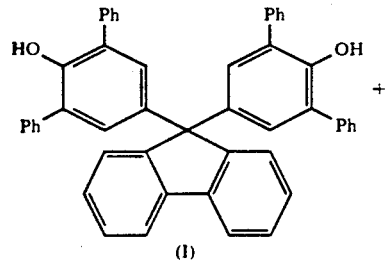

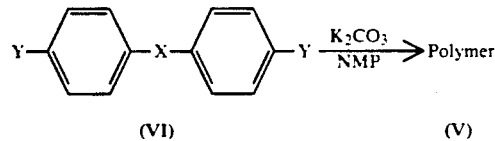

in which Ph and X are as defined above and each Y is a fluorine or chlorine atom, preferably a fluorine atom.

The nucleophilic substitution is suitably carried out using a stoichiometric ratio of the monomers, in a polar, aprotic solvent in the presence of potassium carbonate at a 20 to 25% solids content and a temperature of 135° to 140° C., for an initial reaction time of 3 to 4 hours, followed by stirring at 160° to 240° C., depending on the solvent used, for a period in excess of 18 hours. Suitable solvents include N,N-dimethylacetamide, N-methyl-2-pyrrolidinone diphenylsulfone and benzophenone.

The initial reaction is suitably carried out under an inert atmosphere, for example, nitrogen or argon, with toluene for the azeotropic removal of water, whereafter the toluene is removed.

The initial reaction is suitably carried out under an inert atmosphere, for example, nitrogen or argon, with toluene for the azeotropic removal of water, whereafter the toluene is removed.

It was expected that the pendant phenyl groups in the compound (I) would produce steric hindrance or poor nucleophilicity in the 3,5-diphenylphen-4-ol moieties, but surprisingly the nucleophilic substitution reaction is found to proceed readily to high molecular weight polymers having a number average molecular weights above 30,000.

The poly(arylene ethers) of formula (V) have inherent viscosities greater than 0.25 dL/g, measured in a 0.5% solution in chloroform at 25° C.; glass transition temperatures in the range of 235° C. to 265° C.; exhibit no weight loss at temperatures below 350° C., with 10% weight loss at temperatures above 550° C.

The polymers are readily soluble in common solvents, for example, chlorinated solvents such as methylene chloride, chloroform and 1,2-dichloroethane, at room temperature. Polymer films can readily be formed from the polymers by casting from solutions.

The effect of the pendant phenyl groups ortho to the ether connecting group is demonstrated by reference to Table I below identifying polymers based on 9,9-bis(4-hydroxyphenyl)fluorene (HPF) and 9,9-bis(3,5-dimethyl-4-hydroxyphenyl)fluorene (DMHPF).

The polymer with no substituents (6), two methyl groups both ortho to the ether oxygen (9) and a polymer of the invention having two phenyl groups both ortho to the ether oxygen (Ex. 5) have Tg values of 223° C., 257° C. and 250° C., which indicates that ortho-substitution with either methyl or phenyl groups causes an increase in Tg. Phenyl groups seem to have less effect on the Tg than methyl groups. However, the thermo-oxidative stability of polymers with pendant phenyl groups is found to be higher than those with methyl groups. It is notable that a polymer of the invention (Ex. 3) has a Tg of 262° C. which is lower than that of the polymer (8) 280° C. and much lower than that of the polymer (10) 310 ° C.

TABLE 1

| Characterization of other Poly(arylene ethers) | | | | |
|---|---|---|---|---|
| dihalide | | PAE | Fluorene | Tg(°C.) | $\eta_{inh}{}^a$ |
| Cl—⌬—C(=O)—⌬—C(=O)—⌬—Cl | | 6 | HPF | 223 | 0.95 |
| Cl—⌬—C(=O)—⌬—Cl | | 7 | HPF | 252 | 1.02 |
| Cl—⌬—S(=O)₂—⌬—Cl | | 8 | HPF | 280 | 0.67 |

TABLE 1-continued

| Characterization of other Poly(arylene ethers) | | | | |
|---|---|---|---|---|
| dihalide | PAE | Fluorene | Tg(°C) | $\eta_{inh}{}^a$ |
| 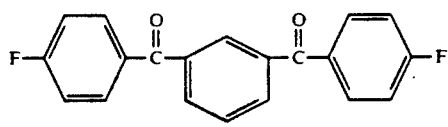 | 9 | DMHPF | 257 | 1.24 |
| 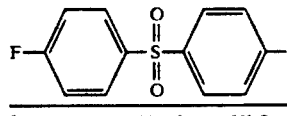 | 10 | DMHPF | 310 | 0.64 |

$^a$0.5% solution in chloroform at 25° C.

The thermal stability of specific poly(arylene ethers) of the invention was characterized by means of thermogravimetric analyses conducted at a heating rate of 10° C/min in air and nitrogen. The TGA values compiled in Table II hereinafter for the degradation temperatures indicate that the polymers derived from 9,9-bis(3,5-diphenyl-4-hydroxyphenyl)fluorene in comparison with those based on the HPF have improved thermostability. For example, 10% weight loss in air for the polymer 6 reportedly occurred at 504° C., whereas for the polymer of Example 5 it took place at 577° C. Furthermore polymers containing methyl groups (see Hergenrother et al POLYMER 1988, 29, 367; Table 9) are considerably less stable in air than in nitrogen as would be expected because methyl groups oxidise in air.

EXAMPLES i) Experimental a) General Methods and Instrumentation

N,N-Dimethylacetamide (DMAc) and N-methyl-2-pyrrolidinone (NMP) were dried over 4 A molecular sieves and toluene was dried over sodium wire. Benzophenone was purchased from Aldrich Chemical Co. (99% pure) and used directly. Differential scanning calorimetry (DSC) and thermogravimetry (TG) were performed on a Seiko SSC5200 thermal analysis system (TG/DTA 220 and DSC 220) with heating rate 10° C. per minute under air or nitrogen. Weight-average molecular weight (Mw) and number-average molecular weight (Mn) of the polymers were obtained on a Waters 510 HPLC apparatus (column: Styragel; eluent:-chloroform). Melting points (mp) were measured on a FISHER-JOHNS melting point apparatus and are uncorrected. Thin-layer chromatography (TLC) was performed on Merck silica gel 60 F$_{254}$ aluminum-backed plates. Flash chromatography was done on silica gel 60 from BDH. Proton nuclear magnetic resonance ($^1$H NMR) spectra were obtained in chloroform-d solution at 200 MHz on a Varian XL-200 FT NMR spectrometer; the 7.24 ppm resonance of residual chloroform in CDCl$_3$ was used as internal reference and chemical shifts are reported in δ units downfield from tetramethylsilane. Carbon nuclear magnetic resonance ($^{13}$C NMR) spectra were obtained at 75.5 MHz on a Varian XL-300 FT NMR spectrometer and are reported in parts per million from tetramethylsilane on the s scale. The following abbreviations are used to describe peak patterns when appropriate: s=singlet, d=doublet, t=triplet, q=quartet, m=multiplet, and br=broad. Mass spectra (MS) were obtained on Du Pont 21-492 B instrument. Microanalyses were done at Guelph Chemical Laboratories Ltd., Ontario, Canada.

b) Materials 1,3-Bis(4-fluorobenzoyl)benzene (1,2-FBB) was prepared by a previously reported procedure and recrystallized twice from toluene (m.p. 179°-180.5° C.). Bis(4-fluorophenyl)ketone (4-FPK) was obtained commercially from Aldrich Chemical Co., Milwaukee, Wis., U.S.A., and recyrstallized from ethanol to yield a white crystalline solid (m.p. 106.5°-107.5° C.). Bis(4-fluorophenyl)sulfone (4-FPS) was purchased from Aldrich Chemical Co. and recrystallized from ethanol to yield a while crystalline solid (m.p. 98°-99° C.). 9,9-Bis(4-hydroxyphenyl)fluorene (9,9-HPF) and 2,6-dipheylphenol (DPP) were obtained from the General Electric Company.

MONOMER SYNTHESES

EXAMPLE 1

9,9-Bis(3,5-diphenyl-4-hydroxyphenyl)fluorene (9,9-DPHPF) and 9-(hydroxyphenyl), 9-(3,5-diphenyl-4-hydroxyphenyl)fluorene from 9,9-bis(4-hydroxyphenyl)fluorene In a 2 L, 3-necked round-bottomed flask equipped with a Vigreux column and a vacuum distillation setup was charged 9,9-DPHPF (75.0 g, 0.20 mol), 2,6-diphenylphenol (DPP; 295 g, 1.20 mol) and 1,2,4-trichlorobenzene (1 L). Methanesulfonic acid (250 mL) was then added and the resulting red suspension was stirred at room temperature. A vacuum was applied and the mixture was slowly heated up to 80° C. At this stage the trichlorobenzene started to reflux and phenol began to distill off. The vacuum distillation was continued for 48 hours and TLC then indicated that the reaction had reached equilibrium. The reaction mixture was cooled to room temperature and it separated into two phases. The top layer was diluted with chloroform (200 mL), neutralized with concentrated sodium carbonate solution and poured slowly into 6 L of petroleum ether. The resulting solids were collected on a filter funnel and the solids were then stirred with cyclohexane (500 mL) in a beaker for 30 min. After filtration, the washed solids weighted 125 g (95%) and contained the desired bisphenol in about 90% yield by HPLC. The remainder was mainly the monotransalkylated phenol 9-(hydroxyphenyl), 9-(3,5diphenyl-4-hydroxyphenyl)fluorene which was isolated in purified form in small quantities by flash chromatography (20% ethyl acetate in hexanes) as white crystals; mp 144°-145° C.; $^1$H NMR 4.79 (br s, 1 H, OH), 5.34 (s, 1 H, OH), 6.70 (d, 2 H, C$_{2,6}$-H on phenol), 7.13 (s, 2 H, C$_{3,5}$-H on DPP), 7.15 (d, 2 H, C$_{3,5}$-H), 7.25-7.50 (m, 16 H, Ar-H), 7.75 (d, 2 H, C$_{4,5}$-H on fluorene); MS (m/e, relative intensity %) 502 (M$^+$·, 10).

EXAMPLE 2

9,9-Bis(3,5-diphenyl-4-hydroxyphenyl)fluorene (9,9-DPHPF) from the methyl ether of 9,9-bis(4-hydroxyphenyl)fluorene The reaction setup was the same as the one used for the synthesis of 9,9-DPHPF from 9,9-bis(4-hydroxyphenyl)fluorene The methyl ether (0.01 mol), DPP (98.5 g, 0.40 mol), methanesulfonic acid (120 mL) and 1,2,4-trichlorobenzene (360 mL) were heated at 80° C. under vacuum for 24 hours. Thin layer chromatography showed that all the ether was converted into 9,9-DPHPF. Following a workup similar to the above, the crude product (58.6 g, 89.5%) was obtained in about 90% purity. After recrystallized from xylene three times, the highly pure 9,9-DPHPF was obtained: 50.5 g (77%); mp 318.4°-322.8° C.; $^1$H NMR 5.33 (s, 2 H , OH), 7.21 (s, 4 H, C$_{3,3',5,5'}$-H on DPP), 7.31-7.58 (m, 26 H, Ar-H), 7.76 (d, 2 H, C$_{4,5}$-H on fluorene); $^{13}$C NMR 65.68, 121.6, 127.3, 128.8, 128.9, 129.2, 129.6, 130.1, 130.7, 131.1, 139.0, 139.6, 141.6, 149.5, 152.7.

ANAL. C$_{49}$H$_{34}$O$_2$ (654.8): Calcd. C, 89.88; H, 5.23. Found: C, 89.94; H, 5.64.

low crystals: 2.653 g (64.7%); mp 191°-192° C.; $^1$H NMR 6.72 (d, 1 H), 7.01 (m, 5 H), 7.16 (m, 6 H), 7.24 (d, 2 H), 7.30-7.49 (m, 4 H), 7.62 (m, 3 H), 7.83 (d, 1 H); MS (EI, m/e, relative intensity %) 410 (M$^+$·, 25), 333 (M$^+$·- Ph, 100).

POLYMERIZATION

The PAE's were prepared by nucleophilic aromatic substitution using a stoichiometric ratio of monomers, a slight excess of potassium carbonate and DMAc or NMP or benzophenone as solvent at 20-25% solids content. The reactions were run initially for about 3-4 hours at 135°-140° C. under nitrogen to azeotrope off water with toluene and then they were stirred at 160°-240° C. (depending on the solvent used) overnight.

EXAMPLE 3

Polymer from 9,9-DPHPF and 1,3-bis(4-fluorobenzoyl)benzene (1,3-FBB)

1,3-FBB (0.492 g, 1.527 mmol), 9,9-DPHPF (1.000 g, 1.527 mmol), and potassium carbonate (0.464 g, 3.359 mmol) in N,N-dimethylacetamide (DMAC; 6.5 mL) and toluene (10 mL) were placed in a round bottom flask equipped with a Dean-Stark trap and condenser under an argon atmosphere. Toluene was used to remove the water formed by azeotropic distillation and the reaction was heated at 135°-145° C. for 3.5 hours. The toluene was then removed and the reaction temperature then rose to 170° C. (oil bath temperature) and was held there for 20 hours. The reaction mixture was allowed to cool to room temperature and diluted with DMAc (5 mL). The solution was poured slowly into methanol (200 mL) containing 10 mL of acetic acid to precipitate the polymer which was washed successively with water and methanol. The polymer was then dissolved in chloroform and the solution was filtered through a sintered glass funnel. The filtrate was added into 200 mL of methanol with stirring to precipitate the polymeric product which was washed with methanol and dried in air. Further drying at 70° C. under vacuum for 18 hours afforded a pale yellow fibrous polymer (1.15 g, 81%). Characterization of the polymers is presented in Table 1.

EXAMPLE 4

Polymer from 9,9-(DPHPF and 4,4'-difluorobenzophenone (4-FPK)

The polymerization was performed in NMP at 160° C. for 18 hours and then at 190° C. for 2 days using 2.0 mmol of monomers. A light yellowish polymer was obtained in 81.6% yield (1.35 g), after purifying twice by dissolving in chloroform and precipitation from methanol.

EXAMPLE 5

Polymer from 9,9-DPHPF and 4,4'-difluorodiphenylsulfone (4-FPS)

Polymerization was carried out in benzophenone at 175° C. for 18 hours and then at 235°-240° C. for 24 hours using 2.0 mmol of monomers. The polymer was obtained as a pale brownish powder in 70.2% yield (1.22 g), after purifying twice by dissolving in chloroform and precipitation from methanol.

TABLE I

Characterization of Poly(arylene ethers)

| Example | Tg (°C.) | $\eta_{inh}^a$ | Mw | Mn | Mw/Mn | Film | TGA (°C.)$^b$ Air | N$_2$ |
|---|---|---|---|---|---|---|---|---|
| 3 | 262 | 0.27 | 97300 | 34800 | 2.79 | brittle, clear | 554 | 546 |
| 4 | 260 | 0.34 | 147900 | 40000 | 3.69 | flexible, clear | 566 | 559 |
| 5 | 250 | 0.43 | 91800 | 51300 | 1.79 | flexible, clear | 577 | 565 |

$^a$0.5% solution in chloroform at 25° C.
$^b$temperatures at 10% weight loss.

The thermogravimetric analyses of these polymers are shown below:

2,6-Diphenylphenol will not react with a ketone or corresponding dihalide to produce a bisphenol and consequently this well known reaction is not available for production of 9,9 bis(3,5-diphenyl-4-hydroxypheyl)-fluorene. In order to demonstrate this the following example was carried out under the usual conditions employing 2,6-diphenylphenol (DPP) and dichlorodiphenylmethane.

EXAMPLE 6

A suspension of DPP (4.921 g, 0.020 mol), dichlorodiphenylmethane (2.371 g, 0.010 mol) and a catalytic amount of phenol (100 mg) in xylene (8.0 mL) was heated to the temperature of reflux (140° C.). After about 7-8 hours the evolution of hydrogen chloride ceased, and the reaction mixture was allowed to cool to room temperature. The resulting yellow solids were collected on the filter funnel and washed with ether. Recrystallization from xylene gave the pyrane below as yellow crystals: 2.653 g (64.7%); mp 191°-192° C.; $^1$H NMR 6.72 (d, 1 H), 7.01 (m, 5H) 7.16 (m,6 H), 7.24 (d, 2 H), 7.30-7.49 (m, 4H), 7.62 (M, 3H), 7.83 (d, 1 H); MS (EI, m/e, relative intensity %) 410 (M$^+$·,25), 333 (M$^+$·- Ph,100).

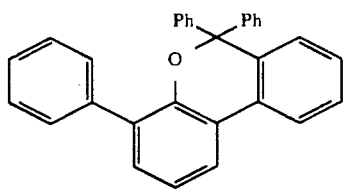
It is clear that the 9,9-dichlorodiphenylfluroene can be expected to react similarly to form a pyran.
We claim:
1. 9,9-Bis(3,5-diphenyl-4-hydroxyphenyl)fluorene.
* * * * *